United States Patent
Cohen

(10) Patent No.: US 11,273,191 B2
(45) Date of Patent: Mar. 15, 2022

(54) ADMINISTERING COMPOSITIONS FOR IMPROVED IMMUNE SYSTEM FUNCTIONING

(71) Applicant: Script Essentials, LLC, Broomfield, CO (US)

(72) Inventor: Suzy Cohen, Broomfield, CO (US)

(73) Assignee: Script Essentials, LLC, Broomfield, CO (US)

(*) Notice: Subject to any disclaimer, the term of this patent is extended or adjusted under 35 U.S.C. 154(b) by 193 days.

(21) Appl. No.: 16/834,351

(22) Filed: Mar. 30, 2020

(65) Prior Publication Data

US 2021/0299197 A1 Sep. 30, 2021

(51) Int. Cl.
| | |
|---|---|
| *A61K 36/00* | (2006.01) |
| *A61K 36/06* | (2006.01) |
| *A61K 36/53* | (2006.01) |
| *A61K 36/63* | (2006.01) |
| *A61K 36/19* | (2006.01) |
| *A61K 9/20* | (2006.01) |
| *A61K 36/539* | (2006.01) |
| *A61K 31/05* | (2006.01) |
| *A61K 9/48* | (2006.01) |
| *A61K 31/145* | (2006.01) |

(52) U.S. Cl.
CPC ............... *A61K 36/06* (2013.01); *A61K 9/20* (2013.01); *A61K 9/48* (2013.01); *A61K 31/05* (2013.01); *A61K 31/145* (2013.01); *A61K 36/19* (2013.01); *A61K 36/539* (2013.01); *A61K 36/63* (2013.01)

(58) Field of Classification Search
None
See application file for complete search history.

(56) References Cited

U.S. PATENT DOCUMENTS

| | | | | |
|---|---|---|---|---|
| 2004/0097584 A1* | 5/2004 | Graus | ............... | A61K 36/28 514/543 |
| 2014/0186456 A1* | 7/2014 | Day | ............... | A61K 31/05 424/535 |
| 2020/0054690 A1* | 2/2020 | Ranganathan | ......... | A23L 33/14 |

FOREIGN PATENT DOCUMENTS

| | | | |
|---|---|---|---|
| CN | 104189879 A | * | 12/2014 |
| CN | 108740369 A | * | 11/2018 |
| ID | 201204358 A | * | 10/2012 |
| KR | 20170048938 A | * | 5/2017 |
| KR | 20190081812 A | * | 7/2019 |

* cited by examiner

*Primary Examiner* — Michael Barker
*Assistant Examiner* — Randall O Winston
(74) *Attorney, Agent, or Firm* — FisherBroyles LLP; Ian R. Walsworth

(57) ABSTRACT

The present disclosure relates to methods of administering a composition to a patient, particularly in the form of a dietary supplement, which addresses immune system deficiencies and promotes healthy immune system functioning. The present disclosure also related to compositions and methods for improving or boosting immune system functioning. The present disclosure further provides novel compositions for balancing immune response in human subjects.

16 Claims, No Drawings

ADMINISTERING COMPOSITIONS FOR IMPROVED IMMUNE SYSTEM FUNCTIONING

FIELD OF THE INVENTION

The present invention is directed to compounds, particularly dietary supplements, used for healthy immune system functioning. The present invention is also directed to methods for improving a person's immune system, as well as methods for formulating and administering a supplement to accomplish the same.

BACKGROUND OF THE INVENTION

Accordingly, there is a long-felt but unresolved need to address these and other problems, which are the subject of the compositions and methods described in detail herein.

SUMMARY OF THE INVENTION

The invention in embodiments relates to a compound, particularly in the form of a dietary supplement, which addresses immune system deficiencies and promotes healthy immune system functioning, and that otherwise addresses the shortcomings in the prior art. As disclosed in more detail in the Detailed Description, the present invention provides compositions and methods for improving or boosting immune system functioning. The present invention comprises novel compositions for balancing immune response in human subjects.

More particularly, the compositions described herein have been shown to activate B cells and strengthen the mucosal immune barrier while activating NK cell activity following consumption. The compositions have also been shown to promote general health and favorable balance of intestinal flora and promote ra more robust immune system response during seasonal variations. In preferred embodiments, these benefits are realized within two hours following consumption of the composition.

The present disclosure also relates to methods of administering a composition to an individual experiencing immune deficiencies. Methods for forming the compound are further described herein.

The composition disclosed herein may further comprise herbs and nutrients to specifically support intestinal health in human subjects, which is beneficial to healthy immune system functioning. By administering various herbs and nutrients, the patient's intestinal system improves, and intestinal health has been shown to improve immune system health. Further, the composition disclosed herein may provide one or more herbals to provide broad-spectrum antiviral, antimicrobial, anti-inflammatory and neuroprotective benefits.

In varying embodiments, the composition further supports the reduction of pro-inflammatory cytokines commonly elevated during illness/sickness, including but not limited to interleukin ("IL")-1b, IL-6 and TNF alpha.

The composition is preferably free of common allergens, such as milk, casein, egg, fish, shellfish, tree nuts, peanuts, wheat, gluten, corn and soybeans. The composition is preferably suitable for consumption by individuals following a vegan and/or vegetarian diet. The composition preferably is devoid of artificial colors and preservatives.

In embodiments, the unique combination of the composition is preferably administered orally in the form of a capsule, tablet, powder or lozenge. The unique combination has synergistic advantages over previously known compositions, all proportioned to provide the most benefit to people affected by the problems described above.

The composition is preferably comprised of a unique and novel formulation in predetermined amounts, and further provides benefits previously unexpected. In a preferred embodiment, the composition is comprised of unique blend of the following components: a dried yeast fermentate, such as fermentate derived from natural *Saccharomyces cerevisiae*; olive leaf extract, such as an extract standardized to 20% Oleuropeins; andrographis extract, which may be derived from both stem and leaf, such as standardized to 10% andrographolides; N-acetylcysteine; skullcap root extract, such as *Scutellaria baicalensis* Georgi (including in root form) derived from 8-12:1 concentrate; and, Trans-Resveratrol, such as derived from 50 mg *Polygonum cuspidatum*. In varying embodiments, the composition is comprised of combinations/sub-combinations of the foregoing. In embodiments, the composition may comprise additional components as described herein.

In one embodiment, the dried yeast fermentate is selected from EpiCor® dried yeast extract. EpiCor® is a registered trademark of Embria Health Sciences.

In embodiments, the composition comprises the following components and variable quantities listed as follows:
1) EpiCor® Yeast Fermentate—between about 250 mg to 750 mg;
2) Olive Leaf 20% Extract—between about 100 mg and about 300 mg;
3) Andrographis Extract—between about 100 mg and about 300 mg;
4) N-acetylcysteine—between about 100 mg and about 300 mg;
5) Skullcap Extract—between about 50 mg and 150 mg;
6) Trans-Resveratrol—between about 12.5 mg and 200 mg;

In embodiments, the composition comprises:
1) 500 mg EpiCor® Yeast Fermentate (from natural *Saccharomyces cerevisiae*);
2) 200 mg Olive Leaf 20% Extract (as standardized to 20% Oleuropeins);
3) 200 mg Andrographis Extract (stem and leaf) (as standardized to 10% andrographolides);
4) 200 mg N-acetylcysteine;
5) 100 mg Skullcap Root Extract (as *Scutellaria baicalensis* Georgi (root) derived from 8-12:1 concentrate);
6) 25 mg Trans-Resveratrol (from 50 mg *Polygonum cuspidatum*);

In one embodiment, the composition is provided as a dietary supplement. In one embodiment, the composition is administered in the form of a vegetable-based capsule, and two capsules are administered daily.

In another embodiment, the composition is administered in the form of a powder, a gummy chew, a tablet, a lozenge or a liquid extract.

In a preferred embodiment, the formulation is unflavored, but in further embodiments, the composition may contain one or more palatability agents to favorably alter the taste of the composition for human consumption.

Methods for treatment of individuals with immune system deficiencies, including but not limited to any of the disorders or deficiencies of the human immune system, are also expressly provided in this disclosure. Methods for administering the supplement described herein are also within the scope of the present disclosure.

In embodiments, methods of formulating the composition are also disclosed herein.

It is to be expressly understood that he above-described embodiments, objectives, and configurations are neither complete nor exhaustive. The Summary of the Invention is neither intended, nor should it be construed as being representative of the full extent and scope of the present invention. Other advantages will be apparent from the disclosure of the invention(s) contained herein.

Embodiments of the present invention are set forth in various levels of detail in the Summary of the Invention, and no limitation as to the scope of the present invention is intended by either the inclusion or non-inclusion of elements in this Summary of the Invention. Additional aspects of the present invention will be readily apparent from the view of one of ordinary skill in the art.

DETAILED DESCRIPTION

Although the following text sets forth a Detailed Description of numerous different embodiments, it should be understood that the legal scope of the description is defined by the words of the claims set forth at the end of this disclosure. The Detailed Description is to be construed as exemplary only, and does not describe every possible embodiment since describing every possible embodiment would be impractical, if not impossible. Numerous alternative embodiments could be implemented, using either current technology or technology developed after the filing date of this patent, which would be encompassed by the scope of the claims.

As used herein, references to "the present invention" or aspects thereof should be understood to mean certain embodiments of the present invention and should not necessarily be construed as limiting all embodiments to a particular description.

As used herein, the phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

Unless otherwise indicated, all numbers expressing quantities, amounts, dimensions, conditions, and so forth used in the specification and claims are to be understood as being modified in all instances by the term "about".

The term "a" or "an" entity, as used herein, refers to one or more of that entity. As such, the terms "a" (or "an"), "one or more" and "at least one" can be used interchangeably herein.

The use of "including," "comprising," or "having" and variations thereof herein is meant to encompass the items listed thereafter and equivalents thereof as well as additional items. Accordingly, the terms "including," "comprising," or "having" and variations thereof can be used interchangeably herein.

It shall be understood that the term "means" as used herein shall be given its broadest possible interpretation in accordance with 35 U.S.C. Section 112(f). Accordingly, a claim incorporating the term "means" shall cover all structures, materials, or acts set forth herein, and all of the equivalents thereof. Further, the structures, materials, or acts and the equivalents thereof shall include all those described in the summary of the invention, brief description of the drawings, detailed description, abstract, and claims themselves.

In varying embodiments described herein, the present invention relates to a compound that improves or enhances immune system functioning or that otherwise addresses immune deficiencies or disorders. Certain elements of the novel compounds and methods for formulating the same are described in varying levels of detail herein.

In embodiments, the composition is comprised of the foregoing elements:

Dried Yeast Fermentate

In a preferred embodiment, the composition comprises at least a Dried Yeast Fermentate (preferably derived from natural *Saccharomyces cerevisiae*), between about 250 mg to 750 mg. In a more embodiment, the composition comprises between about 400 and 600 mg of EpiCor® Yeast Fermentate. In a most preferred embodiment, the composition comprises about 500 mg of EpiCor® Yeast Fermentate (derived from natural *Saccharomyces cerevisiae*).

Olive Leaf Extract;

Olive Leaf Extract has been shown to have beneficial effect on the human immune system, particularly when taken in combination with the other components described herein.

In a preferred embodiment, the composition comprises Olive Leaf 20% Extract, preferably standardized to 20% Oleuropeins, between about 100 mg and about 300 mg. In a more preferred embodiment, the composition comprises between about 160 and 240 mg of Olive Leaf 20% Extract. In a most preferred embodiment, the composition comprises about 200 mg of Olive Leaf 20% Extract (standardized to 20% Oleuropeins).

Andrographis Extract

Andrographis Extract has also been found to improve immune system function. In a preferred embodiment, the composition comprises Andrographis Extract, preferably as standardized to 10% andrographolides, between about 100 mg and about 300 mg. In a more preferred embodiment, the composition comprises between about 160 and 240 mg of Andrographis Extract. In a most preferred embodiment, the composition comprises about 200 mg of Andrographis Extract (as standardized to 10% andrographolides).

N-acetylcysteine

In a preferred embodiment, the composition comprises N-acetylcysteine between about 100 mg and about 300 mg. In a more preferred embodiment, the composition comprises between about 160 and 240 mg of N-acetylcysteine. In a most preferred embodiment, the composition comprises about 200 mg of N-acetylcysteine.

Skullcap Root Extract

In a preferred embodiment, the composition comprises Skullcap Root Extract between about 50 mg and 150 mg. In a more preferred embodiment, the composition comprises between about 80 and 120 mg of Skullcap Root Extract. In a most preferred embodiment, the composition comprises about 100 mg of Skullcap Root Extract, preferably as *Scutellaria baicalensis* Georgi (in root form) derived from 8-12:1 concentrate.

Trans-Resveratrol

Trans-Resveratrol has been found through experimentation to provide significant benefits to immune system functioning, particularly when provided in combination with the foregoing components. Resveratrol significantly reduces inflammatory cytokines that may reduce insulin and other natural productions of the human body. Further, Resveratrol has been found to assist in the balancing of healthy cholesterol ratios and reduce cardiovascular complications in human subjects.

Resveratrol is a powerful antioxidant, may reduce pain, fatigue and swelling, and may reduce the risk of cancer in human subjects. Resveratrol has also shown special benefits to individuals who also suffer from diabetes, are at risk of diabetes, or exhibit pre-diabetic symptoms.

*Polygonum cuspidatum* is the botanical name of Japanese knotweed, which in a preferred embodiment is provided as the form of the compound "Resveratrol." This particular form assists with protection of ACE 2 receptors in the lungs, a known attachment site for Coronavirus and other viral infections, which enables rapid spreading.

In a preferred embodiment, the composition comprises between about 12.5 mg and 200 mg of Trans-Resveratrol, preferably from *Polygonum cuspidatum*. In a more preferred embodiment, the composition comprises between about 15 and 50 mg of Trans-Resveratrol. In a most preferred embodiment, the composition comprises about 25 mg of Trans-Resveratrol (from *Polygonum cuspidatum*).

Absent Elements

In addition, the composition of a preferred embodiment is substantially free of the following common allergens: milk, casein, gluten, wheat, eggs, peanuts, tree nuts, dairy, corn, soybeans, sugar and fish/shellfish. The composition preferably does not contain artificial colors, flavors, or preservatives, and is free from magnesium stearate (a common lubricant used in the manufacture of pharmaceuticals and dietary supplements).

Additional Elements

In varying embodiments, the composition can further comprise variances, particularly with respect to encapsulation and/or powder formulations. According to certain embodiments, the compositions described herein can further be provided with one or more palatability agents. These palatability agents serve to add flavor to the composition so that an effective dosage is easier to be ingested. It is within the scope of the present invention that any safe, flavor enhancing palatability agent can be used in a composition of the present invention. Particularly suitable palatability agents for use in the composition of the present invention include, but are not limited to, plant oils, plant hydrolysates, yeast, yeast hydrolysates, and combinations thereof.

Methods

An aspect of the invention is a method to treat a patient experiencing vision impairment, blurry vision, dry eyes, presbyopia, macular edema, cataracts, glaucoma, macular degeneration and temporal arteritis, among other conditions, with a composition comprising a unique combination and blend of Dried Yeast Fermentate (from natural *Saccharomyces cerevisiae*), Olive Leaf Extract (as standardized to 20% Oleuropeins), Andrographis Extract (as standardized to 10% andrographolides), N-acetylcysteine, Skullcap Extract (as *Scutellaria baicalensis* Georgi derived from 8-12:1 concentrate), and Trans-Resveratrol (from *Polygonum cuspidatum*), or combinations/sub-combinations thereof. According to one embodiment, during administration the patient is treated by providing an effective amount of the composition. In certain embodiments, the composition can be taken by the patient daily, with no regard to meals or time of day ingested. In a preferred embodiment, the composition is administered approximately 30 minutes prior to consumption of daily meals, or more than 2 hours following the patient's last meal. In one such embodiment, the composition is administered in the form of a capsule or two capsules that are fit for human consumption.

According to another embodiment, a method to prepare a compound is disclosed. The components are mixed in a proprietary blend and may be provided in a delivery device, for example, in the form of a capsule, tablet, lozenge or powder. The foregoing detailed description of the preferred embodiments is incorporated by reference in this portion of the specification.

While various embodiments of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims. Ranges have been discussed and used within the forgoing description. One of skill in the art will understand that any sub-range within the stated range would be suitable, as would any number within the broad range, without deviating from the spirit of the present invention.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment.

The invention claimed is:

1. A method of treating a patient with an immune system deficiency, comprising:
- administering to the patient with a capsule, wherein the capsule comprises:
  - from about 250 to 750 mcg of Yeast Fermentate;
  - from about 100 to 300 mg the Olive Leaf Extract; and
  - from about 100 to 300 mg of Andrographis Extract;
  - from about 100 to 300 mg N-acetylcysteine;
  - from about 50 to 150 mg Skullcap Root Extract; and
  - from about 12.5 to 200 mg Trans-Resveratrol,
  - wherein the immune system deficiency is Hashimoto's disease.

2. The method of claim 1, wherein the composition is administered to the patient in the form of a dietary supplement.

3. The method of claim 1, wherein the composition is administered to the patient in the form of an acid resistant capsule.

4. The method of claim 1, wherein the composition is administered orally in the form of a tablet.

5. The method of claim 1, wherein the composition administered to the patient further comprises a palatability agent.

6. The method of claim 5, wherein the palatability agent is at least one of a plant oil, plant hydrolysates, yeast, and yeast hydrolysates, and combinations thereof.

7. The method of claim 1, wherein the composition administered to the patient does not include milk, casein, gluten, wheat, eggs, peanuts, tree nuts, dairy, corn, soybeans, sugar and fish/shellfish.

8. The method of claim 1, wherein the Trans-resveratrol is provided in the form of *Polygonum cuspidatum*.

9. A method of improving immune system functioning in a patient exhibiting disorders relating to the same, wherein the method comprises administering a composition consisting essentially of:
- 500 mg of Dried Yeast Fermentate;
- 200 mcg of Olive Leaf Extract;
- 200 mg of Andrographis Extract;
- 200 mg of N-acetylcysteine;

100 mg of Skullcap Root Extract; and
25 mg of Trans-Resveratrol;
wherein the patient is exhibiting Hashimoto's disease.

10. The method of claim 9, wherein the Trans-Resveratrol is selected from 50 mg *Polygonum cuspidatum*.

11. The method of claim 9, wherein the composition administered to the patient is devoid of the following: milk, casein, gluten, wheat, eggs, peanuts, tree nuts, dairy, corn, soybeans, sugar and fish/shellfish.

12. The method of claim 9, wherein the composition is administered to the patient in the form of a dietary supplement.

13. The method of claim 9, wherein the composition is administered to the patient in the form of an acid resistant capsule.

14. The method of claim 9, wherein the composition is administered orally in the form of a tablet.

15. The method of claim 9, wherein the composition further comprises at least one palatability agent.

16. The method of claim 15, wherein the palatability agent is at least one of a plant oil, plant hydrolysates, yeast, and yeast hydrolysates, and combinations thereof.

* * * * *